United States Patent [19]

Mendiratta et al.

[11] Patent Number: 4,547,596

[45] Date of Patent: Oct. 15, 1985

[54] SEPARATION AND RECOVERY OF ALKYLATED PHENOLS

[75] Inventors: Ashok K. Mendiratta, Schenectady; John J. Talley, Clifton Park, both of N.Y.

[73] Assignee: General Electric Company, Schenectady, N.Y.

[21] Appl. No.: 666,400

[22] Filed: Oct. 30, 1984

Related U.S. Application Data

[63] Continuation-in-part of Ser. No. 480,561, Mar. 30, 1983, abandoned.

[51] Int. Cl.[4] .................. C07C 37/72; C07C 37/70
[52] U.S. Cl. .................................. 568/751; 568/756; 568/762
[58] Field of Search ............... 568/750, 751, 756, 762

[56] References Cited

U.S. PATENT DOCUMENTS

| | | | |
|---|---|---|---|
| 3,691,238 | 9/1972 | Biller et al. | 568/756 |
| 3,894,095 | 7/1975 | Pietzsch et al. | 568/756 |
| 4,101,590 | 7/1978 | Sato et al. | 568/756 |
| 4,267,391 | 5/1981 | Leston | 568/751 |
| 4,267,392 | 5/1981 | Leston | 568/751 |
| 4,275,246 | 6/1981 | Greco | 568/752 |
| 4,420,643 | 12/1983 | Savides et al. | 568/756 |

FOREIGN PATENT DOCUMENTS

| | | | |
|---|---|---|---|
| 2637923 | 3/1978 | Fed. Rep. of Germany | 568/756 |
| 138766 | 11/1979 | German Democratic Rep. | 568/751 |
| 29139 | 8/1976 | Japan | 568/756 |
| 697476 | 9/1953 | United Kingdom | 568/751 |
| 194101 | 5/1967 | U.S.S.R. | 568/751 |
| 343970 | 8/1972 | U.S.S.R. | 568/756 |
| 727613 | 4/1980 | U.S.S.R. | 568/756 |

Primary Examiner—Werren B. Lone
Attorney, Agent, or Firm—Richard J. Traverso; James C. Davis, Jr.; James Magee, Jr.

[57] ABSTRACT

A method is provided for separating alkylated phenols based on differences in their dissociation constants without the consumption of neutralizing acid or base. This is accomplished by selectively reacting the mixed alkylated phenol having the having dissociation constant to the salt form and isolating the salts from the mixture in an aqueous solution. The alkylated phenols are then recovered from the aqueous solution in unreacted form with an organic solvent. Essentially all solvents and solutions can be recycled.

8 Claims, No Drawings

SEPARATION AND RECOVERY OF ALKYLATED PHENOLS

This is a continuation-in-part of application Ser. No. 480,561, filed Mar. 30, 1983, now abandoned.

This invention relates to a method of separating alkylated phenols based on the differences in their dissociation constants and recovering said alkylated phenols from solution. More particularly, this invention relates to a method of separating mixed alkylated phenols by selectively reacting the alkylated phenol having the higher dissociation constant to the corresponding salt with a base, separating the reacted alkylated phenol, and extracting the reacted alkylated phenol with an organic solvent to recover the alkylated phenol.

BACKGROUND OF THE INVENTION

The separation of some mixed alkylated phenols is very difficult when applying common separation methods, such as, distillation, extraction, crystallization, etc.; due to their close boiling points, polarities and densities. It has been found that some mixtures of alkylated phenols can be separated based on the differences in their dissociation constants utilizing dissociation extraction techniques.

The conventional dissociation extraction techniques require the alkylated phenols be in a water-immiscible organic solvent which is treated with a strong basic aqueous solution to selectively neutralize the alkylated phenol having the higher dissociation constant and form an ionized salt. The alkylated phenol in salt form is absorbed into the aqueous phase. The aqueous phase is then separated from the organic phase and treated with a mineral acid to regenerate the alkylated phenol from the ionized salt form. Hence, conventional dissociation extraction techniques present disadvantages in the continual consumption of strong base and mineral acid, in the handling of mineral acid and in the production of waste water.

The process comprising this invention overcomes the disadvantages of continual consumption of acid and base, the continual production of waste water and the handling of acid when separating alkylated phenols based on the differences in their dissociation constants.

SUMMARY OF THE INVENTION

This invention concerns a method of separating alkylated phenols utilizing a dissociation-extraction technique without consumption of acid or base. It involves contacting a mixture of alkylated phenols within a water-immiscible organic solvent with an aqueous solution containing a base. The base in the aqueous solution reacts preferentially with the alkylated phenol having a higher dissociation constant to form an ionic salt. The aqueous solution retains the reacted alkylated phenol in salt form.

The alkylated phenol (or phenols) is then recovered from this basic aqueous solution in an "unreacted" form without neutralization and reversal of the ionization reaction with an acid.

The basic aqueous solution containing the water soluble salt of the alkylated phenols is contacted with a water-immiscible organic solvent in which the alkylated phenols are soluble to extract the reacted alkylated phenol and then the basic aqueous solution is separated from said water-immiscible organic solvent. The water-immiscible organic solvent is selected from a group which provides a good solvent medium for the alkylated phenols. The reacted alkylated phenol can then be recovered from the organic extracting solvent and the unreacted alkylated phenol can be recovered from the organic solvent which contained the mixture of alkylated phenols.

The organic extraction solvent and the organic solvent which contained the mixture of alkylated phenols can be recycled back into the process after the alkylated phenols are removed. The aqueous solution can also be recycled since the extraction of the reacted alkylated phenol regenerates the base within the aqueous solution. Essentially all solvents are recyclable in this process.

Mineral acids are not utilized to regenerate the reacted alkylated phenol from the salt form and no waste water is produced by the neutralization of the salt with acid. In addition, this process can be performed utilizing multi-stage counter current procedures, which maximizes the extent of separation of the mixed alkylated phenols and the recovery of the reacted alkylated phenol from the aqueous solution.

OBJECTS OF THE INVENTION

An object of the present invention is to provide an improved method of separating alkylated phenols based on their dissociation constants.

Another object of the present invention is to provide a method for separating alkylated phenols, based on their dissociation constants, without consuming acid and base.

Another object of the present invention is to provide a method of separating alkylated phenols, based on their dissociation constants, where all solvents utilized are recyclable.

Another object of the present invention is to provide a method of recovering alkylated phenols from a basic aqueous solution without consuming acid or base.

Another object of the present invention is to recover alkylated phenols from a basic aqueous solution without reacting the salt form of the alkylated phenols with acid by utilizing a water immiscible organic extracting solvent.

DETAILED DESCRIPTION OF THE INVENTION

The present invention is directed to a process for separating alkylated phenols based on the differences in their acidic strengths, i.e., dissociation constants. The term "alkylated phenol", as used herein, refers to alkyl substituted monomeric phenols, including monohydroxy benzenes and dihydroxy benzenes, and alkyl substituted bisphenols. The mixed alkylated phenols which can be effectively separated by this process typically have appreciable differences in their acidic strengths. These include mixtures of 2,6-xylenol and para-cresol and mixtures of 2,3,5-trimethylphenol and 2,3,6-trimethylphenol. This process is also capable of separating mixed alkylated phenols which do not have large differences in their acidic strengths. However, the separation of such mixtures by this process is not as effective when separating mixtures of alkylated phenols having large differences in their dissociation constants.

The mixed alkylated phenols must be within a water immiscible organic solvent in which they are soluble for separation to occur. Suitable solvents include toluene, xylene, benzene, etc. Besides providing a good solvent medium for the alkylated phenols and being insoluble in water; the solvent must not react when in the presence of high concentrations of base. It is preferable to utilize organic solvents which have boiling points sufficiently distinct from that of the alkylated phenols so that subsequent recovery of the alkylated phenols can be accomplished by distillation. When separating mixtures of 2,6-xylenol and paracresol and mixtures of 2,3,5-trimethylphenol and 2,3,6-trimethylphenol, an organic solvent principally comprised of toluene is preferred.

The quantity of organic solvent utilized to dissolve the alkylated phenols is not critical for the separation to occur. A suitable quantity of organic solvent is that necessary to form a 7:3 weight ratio of solvent to alkylated phenols. The use of larger quantities of organic solvent is permitted and the use of smaller quantities of organic solvent will also allow separation to occur. It is preferable to utilize only a quantity necessary to dissolve the alkylated phenols.

The organic solvent containing the alkylated phenols is contacted with an aqueous solution containing a base. The alkylated phenol having a higher dissociation constant preferentially reacts with the base to form the corresponding salt, leaving a substantial portion of the alkylated phenol with the lower dissociation constant unreacted. The alkylated phenol in salt form remains in the aqueous solution once contact is complete and is isolated from the unreacted alkylated phenol within the organic solvent.

The base present within the aqueous solution is preferably sodium hydroxide, but any base sufficiently strong to neutralize the alkylated phenol having the higher dissociation constant is suitable. The quantity of base that should be present within the aqueous solution is dependent on the number of moles of alkylated phenol having the higher dissociation constant present within the organic solvent. It is preferable to utilize a quantity of base equivalent to the stoichiometric quantity that is necessary to neutralize all of the alkylated phenol with the higher dissociation constant. When the quantity of base within the aqueous solution is above or below the stoichiometric quantity necessary to react with all of the alkylated phenol having the higher dissociation constant, the extent of alkylated phenol separation is reduced. If excess base is present in the aqueous solution, a substantial portion of the alkylated phenol having a lower dissociation constant will remain mixed with the alkylated phenol having a higher dissociation constant. With a deficient quantity of base present in the aqueous solution, a substantial portion of alkylated phenol having a higher dissociation constant will remain mixed with the alkylated phenol having a lower dissociation constant. Where sodium hydroxide is utilized, it is preferable to maintain a 1:1 molar ratio of sodium hydroxide to the alkylated phenol having a higher dissociation constant so as to completely neutralize this alkylated phenol.

The volume of aqueous solution utilized is not critical for the process to provide separation of alkylated phenols. It is preferable to utilize the quantity of aqueous solution sufficiently large to dissolve all of the alkylated phenol in salt form that is produced by the reaction with base. A volume of aqueous solution equivalent to the volume of organic solution containing alkylated phenols is suitable.

Where there are more than two mixed alkylated phenols, it is necessary to either neutralize more than one alkylated phenol or leave more than one alkylated phenol unreacted. Separation only occurs between those alkylated phenols which are neutralized and those alkylated phenols which remain unreacted. No separation takes place between pairs of neutralized alkylated phenols or pairs of unreacted alkylated phenols. To separate the alkylated phenols within these pairs, the isolated pair may be treated in accordance with this process, where their dissociation constants are distinct.

To increase the selectivity of the reaction with base and alkylated phenol having the higher dissociation constant and to maximize the separation of the reacted alkylated phenol from the unreacted alkylated phenol, multi-stage counter-current extraction procedures can be performed. With multi-stage counter-current extraction procedures, the use of a stoichiometric quantity of base necessary to completely react the alkylated phenol having the higher dissociation constant, provides the best results. One means for performing these counter-current procedures is to utilize a tubular column fitted with equally spaced agitators along its length and feed the aqueous solution and organic solvent at opposing ends. These multi-stage counter-current procedures essentially function as a series of extraction operations to provide greater ionization selectivity and separation between alkylated phenols than a single stage extraction.

After the organic solvent and aqueous solution have been contacted, the organic phase contains unreacted alkylated phenols and the aqueous phase contains reacted alkylated phenols. The organic solvent phase is separated from the aqueous phase and the unreacted alkylated phenol is recovered. This can be accomplished by any means suitable for the particular organic solvent and alkylated phenols concerned. Where toluene is the organic solvent and 2,6-xylenol or 2,3,6-trimethylphenol is the alkylated phenol, distillation is preferred. When the alkylated phenol is removed from the organic solvent phase, the solvent is suitable for recycling back to the process to dissolve a mixture of two or more alkylated phenols to be separated by this process once again.

The aqueous phase contains all or a substantial portion of the alkylated phenols which reacted with the base. These alkylated phenols are in the salt form which makes them water-soluble. Surprisingly, these alkylated phenols can be extracted from the aqueous phase with another organic solvent. The organic solvent utilized must be immiscible in water and must provide a good solvent medium for the alkylated phenol. A simple extraction procedure, such as contacting the basic aqueous solution with the water-immiscible organic solvent and separating said water-immiscible organic solvent from said basic aqueous solution, is all that is necessary.

Any alkylated phenol which provides a water-soluble salt upon reaction with base is suitable for recovery by this procedure. Examples of suitable alkylated phenols include monomeric phenols having 1–5 hydrocarbon radicals of from 1 to 4 carbon atoms with up to 12 carbon atoms for the complete molecule. Suitable alkylated bisphenols are those having 1 to 10 hydrocarbon radicals of from 1 to 4 carbon atoms with up to 24 carbon atoms for the complete molecule.

The alkylated monomeric phenols which are preferred are those having from 1 to 3 methyl radicals and the preferred alkylated bisphenols are those with a hydrocarbon bridge between the phenyl nuclei of from about 1 to 3 carbon atoms, having from 0–4 methyl radicals, and those with the phenyl nuclei linked directly, having 1 to 4 methyl radicals.

The alkylated phenols which are most preferred include para-cresol, 2,3,5-trimethyl phenol, ortho-cresol, meta-cresol, 2,3,6 trimethyl phenol, 2,4,6-trimethyl phenol, 3,4,5 trimethyl phenol, 2,6 xylenol, 2,4 xylenol, 2,5 xylenol, 2,3 xylenol, 3,5 xylenol, 2,4,(4,4' dihydroxydiphenyl) propane and 3,3', 5,5' tetramethyl 4,4' dihydroxy biphenyl.

Organic solvents which are both water-immiscible and provide a suitable solvent medium for the one or more alkylated phenols include aliphatic ketones of from 5 to 13 carbon atoms, cyclic ketones of from 6 to 13 carbon atoms, aromatic ketones of from 8 to 13 carbon atoms. In addition, aliphatic esters and diesters of from 4 to 13 carbon atoms are suitable where they do not have additional polar end groups on the molecule. Those ester species which have hydroxyl groups, carboxyl groups, aldehyde, ketone or ether function groups are unsuitable because of their high solubility in water. Straight chained monohydroxy aliphatic alcohols of from 4 to 13 carbon atoms and branched chained monohydroxy aliphatic alcohols of from 5 to 13 carbon atoms which have a chain length of at least 4 carbon atoms can also be used. Cyclic alcohols of from 5 to 13 carbon atoms are also suitable. Of the aliphatic hydrocarbon organic solvents, suitable species include: halogenated-hydrocarbons having 1 to 13 carbon atoms and nitro-hydrocarbons having 1 to 13 carbon atoms. Of the cyclic hydrocarbon organic solvents, the halogenated species having 4 to 13 carbon atoms are suitable. Of the aromatic hydrocarbons, unsubstituted hydrocarbons, halogenated hydrocarbons and nitro-hydrocarbons of from 6 to 13 carbon atoms are all suitable.

The solvents defined above do not exhaust the list of solvents which can be utilized to achieve the objects of this invention. Although the list of solvents above and these definitions do encompass the solvents which are preferred, a small number of suitable solvents are expected to fall outside of these definitions. These solvents are deemed equivalent to those defined where they are immiscible in water and provide a good solvent medium for the alkylated phenols.

Specific examples of suitable ketones include: methyl n-propyl ketone, diethyl ketone, 4 methyl-3-penten-2-one, cyclohexanone, methyl isobutyl ketone, methyl n-butyl ketone, ethyl n-butyl ketone, 2 heptanone, methyl phenyl ketone, 2 octanone, isophorone, diisobutyl ketone and the like.

Specific examples of suitable esters include: ethyl acetate, γ-valerolactone, n-propyl acetate, isopropyl acetate, n-butyl acetate, sec butyl acetate, isobutyl acetate, diethyl carbonate, amyl acetate, 1,3 dimethyl butyl acetate, ethylene glycol diacetate, diethyl oxylate, 2 ethyl hexyl acetate and the like.

Specific examples of suitable alcohols include: n-butyl alcohol, sec-butyl alcohol, isobutyl alcohol, amyl alcohol, 3-pentanol, isoamyl alcohol, n-hexyl alcohol, 4 methyl-2-pentanol, 2-ethyl butyl alcohol, cyclohexanol, methyl cyclohexanol, 3-heptanol, 1-octanol, 2-ethyl hexanol, diisobutyl carbinol and the like.

Specific examples of unsubstituted hydrocarbons include: benzene, toluene, xylene, ethyl benzene, isopropyl benzene, and the like.

Suitable halogenated hydrocarbons specifically include methylene chloride, ethyl chloride, ethylene chloride, n-butyl chloride, ethylidene chloride, amyl chloride, mono chloro benzene, propylene chloride, chloroform, chloro toluene, trichloroethylene, trichloro ethane, trichloro fluoro methane, dichloro pentane, 2 ethyl hexyl chloride, carbon tetra chloride, tetrachloro ethane, dichloro isopropyl ether, trichloro benzene, o-dichloro benzene and the like.

Specific nitro-hydrocarbons which are suitable include: nitro methane, nitro ethane, 1-nitro propane, 2-nitro propane, benzonitrile and the like.

The lists of suitable organic solvents provided above are not considered to be exhaustive. Other organic solvents which are immiscible in water and solubilize alkylated phenols are deemed to be equivalent to the species recited above.

The extent of extraction is dependent on the organic solvent utilized. Organic solvents of high polarity are often capable of extracting larger quantities of certain alkylated phenols than organic solvents of low polarity. For example, in a single stage extraction toluene can be expected to extract less than 2% of para-cresol in non-ionized form, while butyl acetate, methyl isobutyl ketone and 1-octanol can be expected to extract up to 30% of para-cresol. Therefore, when extracting para-cresol, these three solvents are preferred.

Not wishing to be bound by theory, it is believed that a substantial portion of the alkylated phenol is in equilibrium, equation 1, between the salt form and the unreacted form when the organic solvent is added to the aqueous phase.

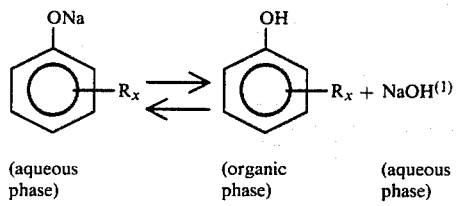

(aqueous phase)  (organic phase)  (aqueous phase)

Where R is an alkyl radical and x is a number from 1 to 5. The equilibrium which results by introducing an organic solvent into the aqueous phase permits some alkylated phenol in unreacted form to be extracted by the organic solvent. The regeneration of base within the aqueous phase, from which alkylated phenol is extracted, also suggests that this equilibrium exists. This regeneration of base within the aqueous phase may place an equilibrium limitation on the extraction of alkylated phenol by the organic solvent. Therefore, a portion of the ionized alkylated phenol may always remain within the aqueous phase.

Extraction of the alkylated phenol from the aqueous phase can be accomplished by any conventional means, such as a single stage batch extraction apparatus, where the organic solvent and aqueous phase are added, mixed and allowed to settle to form two phases. To increase the extent of extraction of alkylated phenol, the contact between the organic solvent and the aqueous phase is maximized by utilizing multi-stage counter-current extraction techniques. By repeatedly mixing and separating new portions of both streams, the multi-stage countercurrent extraction technique functions as a series of single stage batch extractions.

Once the alkylated phenol is recovered from the aqueous phase, the alkylated phenol can be removed from the organic solvent by any conventional means suitable for the particular alkylated phenol and organic solvent concerned. Distillation is preferred where the alkylated phenol is either para-cresol or 2,3,5-trimethylphenol and the organic solvent is selected from the group consisting of 1-octanol, 2-ethylhexanol, benzonitrile, toluene, xylene and o-dichlorobenzene. Upon separation of the alkylated phenol, the organic solvent is suitable for recycling back into the process to further extract alkylated phenol from the separated aqueous phase.

The regeneration of base within the aqueous phase provides an advantage in that, the aqueous phase is suitable for recycling back into the process to selectively react with more alkylated phenol within a mixture. This aqueous phase of regenerated base may contain a residual amount of alkylated phenol in salt form due to the incomplete extraction by the organic solvent. However, this does not effect the suitability of this aqueous phase for recycling back into the process. By controlling the process variables, the extent of reaction between alkylated phenol and base can equal the extent of alkylated phenol extraction by the organic solvent. Under these conditions a steady state is reached and there is virtually no consumption of organic solvents or base.

This process can be performed at room temperature and atmospheric pressure. In addition, higher temperatures and pressures may also be suitable.

In order that those skilled in the art may better understand this invention, the following examples are given by way of illustration and not by way of limitation.

EXAMPLE 1

This example demonstrates the selectivity of the neutralization and extraction of alkylated phenol with the higher dissociation constant within a mixture of alkylated phenols by a base. A mixture of paracresol and 2,6-xylenol of equal weight were separated by first dissolving the mixture in a sufficient quantity of toluene to form a solution containing 15 weight percent of para-cresol and 2,6-xylenol, respectively. This solution was placed in a single stage batch extraction apparatus with an equal weight of 1.5 molar aqueous sodium hydroxide solution at room temperature and then agitated. Upon settling, two phases formed and were separated. The organic phase had a 2,6-xylenol to para-cresol ratio of 10:1 (by weight) with 2,6-xylenol recovery of approximately 75%.

EXAMPLE 2

This example demonstrates the selectivity of the neutralization and extraction of alkylated phenol with the higher dissociation constant from a mixture of alkylated phenols by a base.

A toluene solution containing 15% (by weight) of 2,3,5- and 2,3,6-trimethylphenols, respectively, was placed in a single stage batch extraction apparatus with an equal weight of 1.5 molar aqueous sodium hydroxide solution at room temperature and agitated. Upon settling, two phases were produced and withdrawn. The recovered organic phase was distilled and found to have a 2,3,6- to 2,3,5-trimethylphenol ratio of approximately 4:1 (by weight) with 2,3,6-trimethylphenol recovery of approximately 55%.

EXAMPLES 3-10

These examples demonstrate the extent of extraction of the alkylated phenol present within the aqueous solution in salt form utilizing various organic solvents. The alkylated phenol is recovered in unreacted form. An aqueous solution was prepared to simulate the aqueous phase obtained from a dissociation extraction utilizing multi-stage counter-current extraction techniques where substantially complete separation of alkylated phenol occurs. This aqueous solution, which contained approximately 15% sodium salt of p-cresol, was contacted with equal weights of eight different organic solvents in a single stage batch apparatus at room temperature and agitated. Upon settling, two phases formed and were separated. The extent of para-cresol recovery from the aqueous solution varied from 1-30% for the different organic solvents tested. The results for Examples 3-10 are presented in Table I.

TABLE I

| Example # | Organic Solvent | % p-cresol Recovery |
|---|---|---|
| 3 | Toluene | 1-2% |
| 4 | Xylene | 1-2% |
| 5 | o-dichlorobenzene | 1-2% |
| 6 | 1-octanol | 30% |
| 7 | 2-ethylhexanol | 15% |
| 8 | benzonitrile | 6% |
| 9 | Butyl Acetate | 28% |
| 10 | Methyl Isobutyl Ketone | 31.0% |

$$\% \text{ p-cresol recovery} = \frac{\text{p-cresol in extracted organic phase}}{\text{p-cresol in aqueous feed in salt form}} \times 100$$

EXAMPLE 11

This example demonstrates the extraction of 2,6 xylenol from a basic aqueous solution of the water-soluble salt form of 2,6 xylenol. To an aqueous solution (50 ml) containing sodium hydroxide (0.6 Og, 0.015 moles) were dissolved 1.22 g (0.01 moles) 2,6 xylenol, generating the salt form of 2,6 xylenol. After the dissolution was complete, the basic aqueous solution was contacted with 50 ml methylene chloride. The 2 phases were stirred for 5 minutes and then allowed to separate. The methylene chloride phase was isolated and a sample was analyzed by vapor phase chromatography. This analysis indicated 6.5% of the 2,6 xylenol was extracted from the basic aqueous solution.

EXAMPLE 12

This example demonstrates the extraction of 2,3,5 trimethylphenol from a basic aqueous solution of the water-soluble salt form of 2,3,5-trimethylphenol. To an aqueous solution (50 ml) containing sodium hydroxide (0.60 g, 0.015 moles) were dissolved 1.36 g (0.01 moles) 2,3,5-trimethylphenol, generating the salt form of 2,3,5-trimethylphenol. After dissolution was complete, the basic aqueous solution was contacted with (50 ml) methylene chloride. The two phases were stirred for 5 minutes and then allowed to separate. The methylene chloride phase was isolated and a samples was analyzed by vapor phase chromatography. This analysis indicated 8.3% recovery of 2,3,5-trimethylphenol.

EXAMPLE 13

This example demonstrates the extraction of 1,4 dihydroxy benzene from a basic aqueous solution containing its water-soluble salt form. To an aqueous solution (50 ml) containing sodium hydroxide (1.0 g, 0.025 moles) were dissolved 1.14 gms (0.01 moles) 1,4 dihydroxybenzene, generating the salt form of 1,4 dihydroxybenzene. This aqueous solution was contacted with methylene chloride by stirring for 5 minutes. Upon separation of the two phases, the methylene chloride phase showed about 1% recovery of 1,4 dihydroxy benzene by vapor phase chromatograph analysis.

What is claimed is:

1. A method of recovering one or more alkylated phenols from a basic aqueous solution containing the water-soluble salt of said alkylated phenols, said method comprising:
   (a) contacting said basic aqueous solution with a water-immiscible organic solvent in which said alkylated phenols are soluble and
   (b) separating said water-immiscible organic solvent from said basic aqueous solution;
   said organic solvent being selected from the group consisting of
   aliphatic esters of from 4 to 13 carbon atoms having no polar end groups,
   straight chained monohydroxy aliphatic alcohols of from 4 to 13 carbon atoms,
   branched chained monohydroxy aliphatic alcohols of from 5 to 13 carbon atoms having a chain length of at least 4 carbon atoms and cyclic alcohol of 5 to 13 carbon atoms,
   said alkylated phenols being selected from the group consisting of monomeric phenols having from 1 to 5 alkyl radicals of from 1 to 4 carbon atoms with up to 12 carbon atoms for the complete molecule, and
   bisphenols having from 1 to 10 alkyl radicals of from 1 to 4 carbon atoms with up to 24 carbon atoms for the complete molecule.

2. A method as in claim 1 wherein said alkylated phenols are selected from the group consisting of ortho-cresol, para-cresol, meta-cresol, 2,6 xylenol, 2,4 xylenol, 2,5 xylenol, 2,3 xylenol, 2,4,6 trimethyl phenol, 2,3,6 trimethyl phenol, 2,3,5 trimethyl phenol, 3,4,5 trimethyl phenol, 2,2(4,4' dihydroxy diphenyl) propane and 3,3',5,5' tetramethyl 4,4' dihydroxy biphenyl.

3. A method as in claim 1 wherein the water immiscible organic solvent is selected from the group consisting of: ethyl acetate, n-propyl acetate, isopropyl acetate, n-butyl acetate, sec butyl acetate, isobutyl acetate, diethyl carbonate, amyl acetate, 1,3 dimethyl butyl acetate, ethylene glycol diacetate, diethyl oxylate, 2 ethyl hexyl acetate, n-butyl alcohol, sec butyl alcohol, isobutyl alcohol, amyl alcohol 3-pentanol, iso-amyl alcohol, n-hexyl alcohol, 4 methyl-2 pentanol, 2-ethyl butyl alcohol, cyclohexanol, methyl cyclohexanol, 3-heptanol, 1-octanol, 2-ethyl hexanol, diisobutyl carbinol.

4. A method of recovering one or more alkylated phenols from a basic aqueous solution containing the water-soluble salt of said alkylated phenols, said method comprising extracting said alkylated phenols from said basic aqueous solution with a water immiscible organic solvent in which said alkylated phenols are soluble, said extracting solvent being selected from the group consisting of o-octanol, 2 ethyl hexanol, and butyl acetate, said alkylated phenols being selected from the group consisting of
   monomeric phenols having from 1 to 5 alkyl radicals of from 1 to 4 carbon atoms with up to 12 carbon atoms for the complete molecule, and
   bisphenols having from 1 to 10 alkyl radicals of from 1 to 4 carbon atoms with up to 24 carbon atoms for the complete molecule.

5. A method of recovering para-cresol from a basic aqueous solution containing the water-soluble salt of said para-cresol, said method comprising:
   (a) contacting said basic aqueous solution with a water-immiscible organic solvent in which said para cresol is soluble and
   (b) separating said water-immiscible organic solvent from said basic aqueous solution;
   said water-immiscible organic solvent being selected from the group consisting of
   aliphatic esters of from 4 to 13 carbon atoms having no polar end groups,
   straight chained monohydroxy aliphatic alcohols of from 4 to 13 carbon atoms,
   branched chained monohydroxy aliphatic alcohols of from 5 to 13 carbon atoms having a chain length of at least 4 carbon atoms and
   cyclic alcohols of from 5 to 13 carbon atoms.

6. A method as in claim 5 wherein the water immiscible organic solvent is selected from the group consisting of: ethyl acetate, n-propyl acetate, isopropyl acetate, n-butyl acetate, sec butyl acetate, isobutyl acetate, diethyl carbonate, amyl acetate, 1,3 dimethyl butyl acetate, ethylene glycol diacetate, diethyl oxylate, 2 ethyl hexyl acetate, n-butyl alcohol, sec butyl alcohol, isobutyl alcohol, amyl alcohol 3-pentanol, iso-amyl alcohol, n-hexy alcohol, 4 methyl-2 pentanol, 2-ethyl butyl alcohol, cyclohexanol, methyl cyclohexanol, 3-heptanol, 1-octanol, 2-ethyl hexanol, diisobutyl carbinol.

7. A method of recovering para-cresol from a basic aqueous solution containing the water-soluble salt of said para-cresol, said method comprising extracting said para-cresol from said basic aqueous solution with a water immiscible organic solvent in which said para-cresol is soluble, said extracting solvent being selected from the group consisting of o-octanol, 2 ethyl hexanol and butyl acetate.

8. A method as in claim 4 wherein the alkylated phenol is selected from the group consisting of para-cresol, 2,3,5-trimethyl phenol and 2,6 xylenol.

* * * * *